(12) United States Patent
Brown

(10) Patent No.: US 7,414,078 B2
(45) Date of Patent: *Aug. 19, 2008

(54) ORAL GENERAL ANESTHETICS AND METABOLITICALLY RESISTANT ANTICONVULSANTS

(75) Inventor: Milton L. Brown, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/283,333

(22) Filed: Nov. 18, 2005

(65) Prior Publication Data

US 2006/0111339 A1    May 25, 2006

Related U.S. Application Data

(63) Continuation of application No. 10/475,545, filed as application No. PCT/US02/11507 on Apr. 15, 2002, now Pat. No. 7,026,358.

(60) Provisional application No. 60/354,181, filed on Feb. 4, 2002, provisional application No. 60/333,603, filed on Nov. 27, 2001, provisional application No. 60/284,040, filed on Apr. 16, 2001.

(51) Int. Cl.
*A61K 31/65* (2006.01)
*C07D 223/10* (2006.01)
*C07D 209/38* (2006.01)
*C07C 233/08* (2006.01)
*C07C 33/46* (2006.01)

(52) U.S. Cl. .......... 514/617; 540/526; 548/485; 564/170; 568/812

(58) Field of Classification Search .......... 540/526; 548/485; 514/617; 564/170; 568/712
See application file for complete search history.

(56) References Cited

U.S. PATENT DOCUMENTS

2005/0228033 A1* 10/2005 Brown .......... 514/376

FOREIGN PATENT DOCUMENTS

DE    2723464 A1 * 12/1977

OTHER PUBLICATIONS

CAS Search Printout for Zelenin et al. Izvestiya Akademii Nauk SSSR, Seriya Khimicheskaya, 1985, 4, 955-6.*
CAS Search Printout for DE2723464A1 is provided.*
Zelenin et al. Izvestiya Akademii Nauk SSSR, Seriya Khimicheskaya 1986, 9, 2080-5; (CAS Abstract Attached).*
Blitz et al. Chem. Lab., Univ. Kiel. Ber. 1908, 41, 1379-93; (CAS Abstract attached).*
Page et al. Tetrahedron 1992, 48(35), 7265-74; (CAS Abstract and structures attached).*

* cited by examiner

*Primary Examiner*—Rebecca L Anderson
*Assistant Examiner*—Jason M Nolan
(74) *Attorney, Agent, or Firm*—Rodney L. Sparks

(57) ABSTRACT

The present invention is directed to novel themisone derivative compounds that have been modified to prevent the formation of the toxic metabolite, 2-phenyl-acrylamide. Compositions comprising such derivative compounds have activity as anesthetics and as neuroprotective agents.

8 Claims, 8 Drawing Sheets

Fig. 2

| Phase I mouse data *i.p.* | National Institute of Neurological Diseases and Stroke *Anti-Epileptic Drug Development Program* | | |
|---|---|---|---|
| | Maximal electroshock (MES) | | |
| | Dose (mg/kg) | Protected animals | Duration of action (hrs) |
| Themisone | 30 | 0/1 | - |
| | 100 | 2/3 | 0.25 |
| | 300 | 1/1 | 0.5 |
| ICM-I-40N(17) | 30 | 0/1 | - |
| | 100 | 3/3 | 4 |
| | 300 | 1/1 | 4 |

Fig. 3

| Phase I mouse data *i.p.* | National Institute of Neurological Diseases and Stroke *Anti-Epileptic Drug Development Program* | | |
|---|---|---|---|
| | Subcutaneous Metrazol (scMet) | | |
| | Dose (mg/kg) | Protected animals | Duration of action (hrs) |
| Themisone | 30 | 0/1 | - |
| | 100 | 5/5 | 0.25 |
| | 300 | 1/1 | 0.5 |
| ICM-I-40N | 30 | 0/1 | - |
| | 100 | 5/5 | 0.5 |
| | 300 | 1/1 | 4 |

Fig. 4

| Phase I mouse data i.p. | National Institute of Neurological Diseases and Stroke *Anti-Epileptic Drug Development Program* | | |
|---|---|---|---|
| | Rotorod neurotoxicity | | |
| | *Dose (mg/kg)* | *Affected animals* | *Duration of toxicity (special comments)* |
| Themisone (structure: NH₂, CH₃, OH) | 30 | 0/4 | - |
| | 100 | 4/8 | 0.25 hrs |
| | 300 | 1/1 | 0.5 hrs |
| ICM-I-40N (structure: NH₂, CF₃, OH) | 30 | 0/4 | - |
| | 100 | 2/4 | 4 hrs (unable to grasp) |
| | 300 | 4/4 | 0.5 hrs (loss of righting) |
| | 300 | 2/2 | 4 hrs (anesthesia) |

Fig. 5
*Phase II*

| mouse data<br>*Oral* | National Institute of Neurological Diseases and Stroke<br>*Anti-Epileptic Drug Development Program* | | |
|---|---|---|---|
| | MES ED$_{50}$ | ScMet ED$_{50}$ | Rotorod TD$_{50}$ |
| ICM-I-40N(17) | 9.92 mg/kg<br>(6.9-13.4) | 38.57 mg/kg<br>(24.6-51.9) | 100 mg/kg |
| Phenytoin | 9.5 mg/kg<br>(8.13-10.4) | >300 mg/kg | 65.5 mg/kg<br>(52.5-72.1) |

ORAL GENERAL ANESTHETICS AND METABOLITICALLY RESISTANT ANTICONVULSANTS

RELATED APPLICATIONS

This application is a continuation of U.S. patent application Ser. No. 10/475,545 filed Oct. 15, 2003, now U.S. Pat. No. 7,026,358 which is a national stage filing of International Application No. PCT/US02/11507, filed Apr. 15, 2002, which claims priority under 35 USC §119(e) to U.S. Provisional Application Ser. Nos. 60/284,040, filed Apr. 16, 2001, 60/333,603, filed Nov. 27, 2001 and 60/354,181, filed Feb. 4, 2002, the disclosures of which are incorporated herein.

FIELD OF THE INVENTION

The present invention is directed to novel derivatives of α-hydroxy-α-methylbenzeneacetamide (themisone), and the use of such derivatives as therapeutic agents. More particularly, compositions comprising the present themisone derivatives car, be administered -for reducing the incidence and severity of seizures and for use as a general anesthetic.

BACKGROUND OF THE INVENTION

Many compositions are available for sedating patients or, in larger dosages, for inducing surgical anesthesia in patients. These materials are used alone or in combination with other agents, such as nitrous oxide, to induce narcosis and to raise the patients pain threshold so that the patient can withstand surgical procedures. Likewise in smaller doses, these materials can reduce anxiety and generally sedate the patient. For example the following compounds are in general use as sedative and anesthetic agents: thiopental sodium, 5-allyl-1-methyl-5-(1-methyl-2-pentynyl)barbituric acid sodium salt (brevitol), 2-bromo-2-chloro-1,1,1-trifloroethane (halothane), and the like.

Most anesthetic and sedative agents, in addition to their beneficial effects, also lower certain body functions, such as respiration, blood pressure and heart action. Lowered body functions may sometimes lead to complications, particularly in older patients and in patients suffering from cardiac and vascular diseases and diseases of the kidneys and liver. Likewise, reduction in blood pressure may also lead to circulatory insufficiency during the surgical procedures which, unless alleviated, may do serious harm even to patients who have previously exhibited no signs of heart, kidney or liver disfunction.

General anesthesia, administered as an inhaled or intravenous agent, for a surgical operation involves analgesia, amnesia, loss of consciousness, motionlessness and abolition of autonomic responses. The mechanism of action is still not completely understood, but most general anesthetics act at multiple molecular sites. The potential mechanisms of anesthesia action include protein receptor, lipid and ion channels. As the solubility of anesthetics increases in oil, so does the potency leading to the lipid theory developed by Meyer and Overton. There is also a correlation between anesthesia potency and the ability of the anesthetic to inhibit the enzyme activity of the protein, for example in firefly luciferase, a model used for studying anesthesia. In addition, potentiation of the inhibitory response, mediated by the neurotransmitter GABA (gamma-aminobutyric acid), dampens neuronal excitability placing the GABA receptor as a potential receptor site for anesthetic action. GABA is the major mediator of inhibitory synaptic transmission, and a family of ligand-gated chloride channel proteins. Other theories include NMDA and ligand-gated ion channels as a receptor. There is sufficient evidence supporting the blockade of $Na^+$ channels and the activation of $K^+$ channels.

The effects of anesthesia depend on the concentration at the site of action, although concentrations cannot be measured in the brain of humans, therefore the concentration in the blood or expired gas (for inhaled anesthetics) is evaluated. Current inhaled general anesthetics (including, halothane enflurane, nitrous oxide, desflurane, isoflurane and sevoflurane, shown below) have a low therapeutic index (usually 2-3), hence the discovery of a new structural class would help in the development of safer anesthetics.

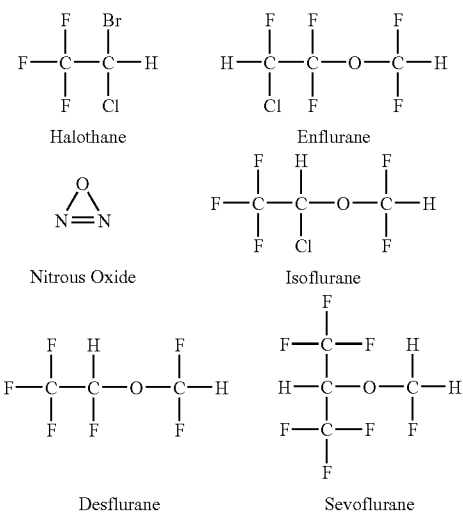

The present invention is directed to derivatives of themisone, that have been found to have anticonvulsant and anesthetic activity. Themisone, also known as Atrolactamide, was found in the 1950's to be a very potent anticonvulsant. The racemic mixture protected 4 out of 4 mice against seizures at 250 mg/kg, however the compound was toxic (blood dyscrasias, rash). Applicants believe the toxicity of this compound results from the formation of 2-phenyl-acrylamide by an elimination reaction as shown below:

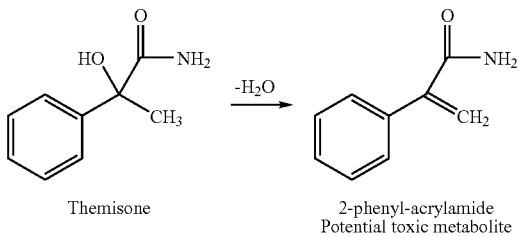

To prevent the formation of this potential metabolite in vivo, applicants have designed and synthesized derivatives of themisone that prevent the elimination and potential formation of 2-phenyl-acrylamide, a potential toxic metabolite. These compounds have been found to exhibit both anti-convulsant activity as well as anesthetic acitivity. Accordingly, one aspect of the present invention is directed to novel themisone derivatives that are blocked from forming 2-phenylacrylamide and the use of such compounds for reducing the incidence and severity of seizures and for use as a general anesthetic.

SUMMARY OF THE INVENTION

The present invention is directed to compounds having a general structure selected from the group consisting of:

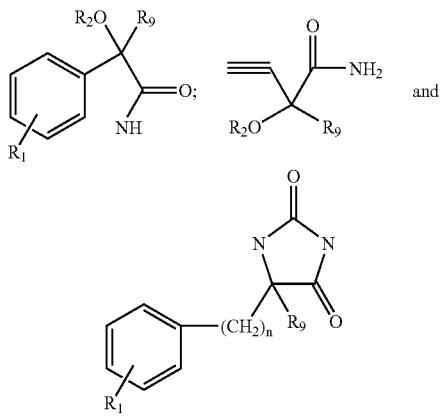

wherein $R_1$ is selected from the group consisting of H, halo, alkyl, haloalkyl, $NH_2$ and $C_1$-$C_4$ alkoxy; $R_2$ is H or alkyl; $R_9$ is optionally substituted aryl or haloalkyl; and n is an integer ranging from 1-3, and the use of such compounds as a sedative/anesthetic or an anticonvulsive agent.

BRIEF DESCRIPTION OF THE DRAWINGS

FIG. 2 is a table listing the data produced during anticonvulsant testing of orally administered themisone and compound 17 in mice. The model examines the compound's ability to stop the spread of seizures induced by a maximal electroshock (MES) test, where corneal electrode implants are primed with a drop of electrolyte solution and an electrical stimulus is delivered for 0.2 second.

FIG. 3 is a table listing the data produced during anticonvulsant testing (using a subcutaneous metrazol test) of intraperitoneal, (i.p.) administered themisone and compound 17 in mice. The subcutaneous metrazol test (scMet) is conducted using a convulsant dose of pentylenetetrazol at the peak effect time of the compound.

FIG. 4 is a table listing the data produced from a toxicity test (TOX). The animals walk on a spinning rod for varying lengths of time to check for the loss of righting reflex or other toxic effects.

FIG. 5 is a table listing the MES $ED_{50}$, ScMet $ED_{50}$ and Rotorod $TD_{50}$ values for mice orally administered either compound 17 or phenytoid.

DETAILED DESCRIPTION OF THE INVENTION

Definitions

Figure 1:
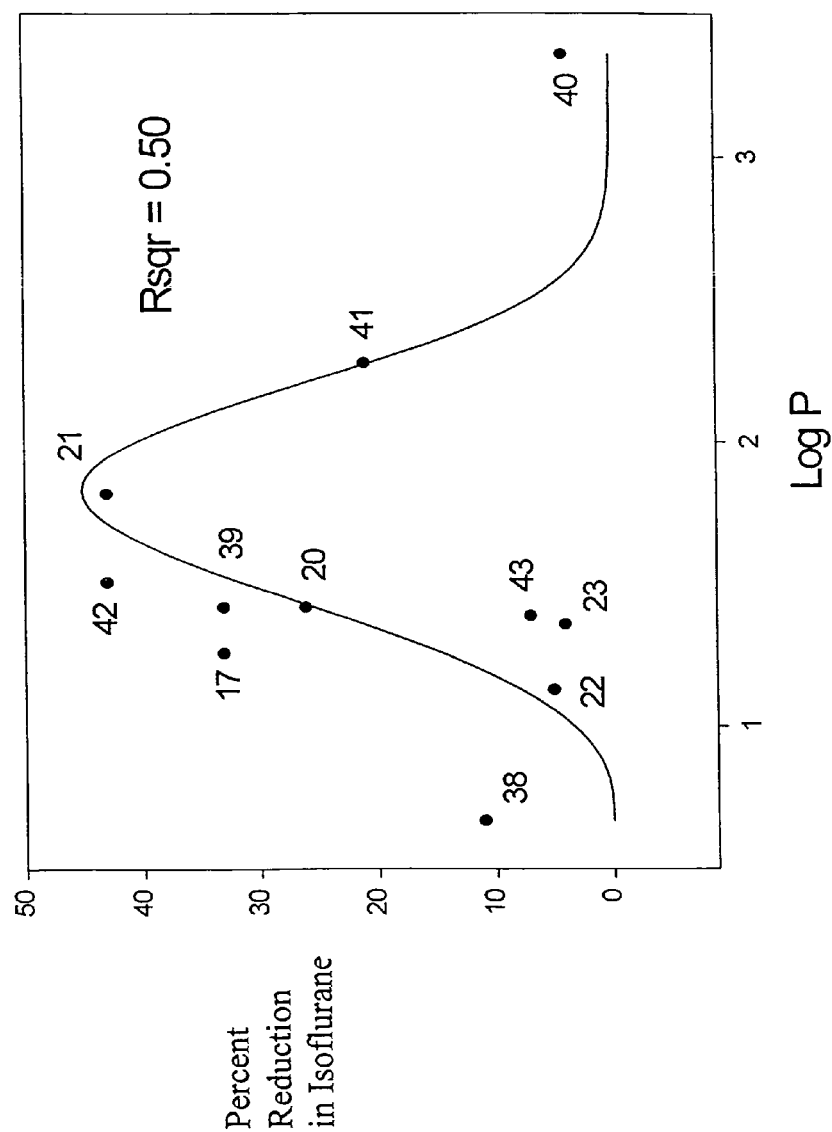
FIG. 1 is a graph plotting the partition coefficient, P (in log P) vs minimum alveolar concentration (MAC) and representing the anesthetic effects of the themisone derivatives (indicated by a reduction in the threshold of Isoflurane anesthesia).
Figure 6:
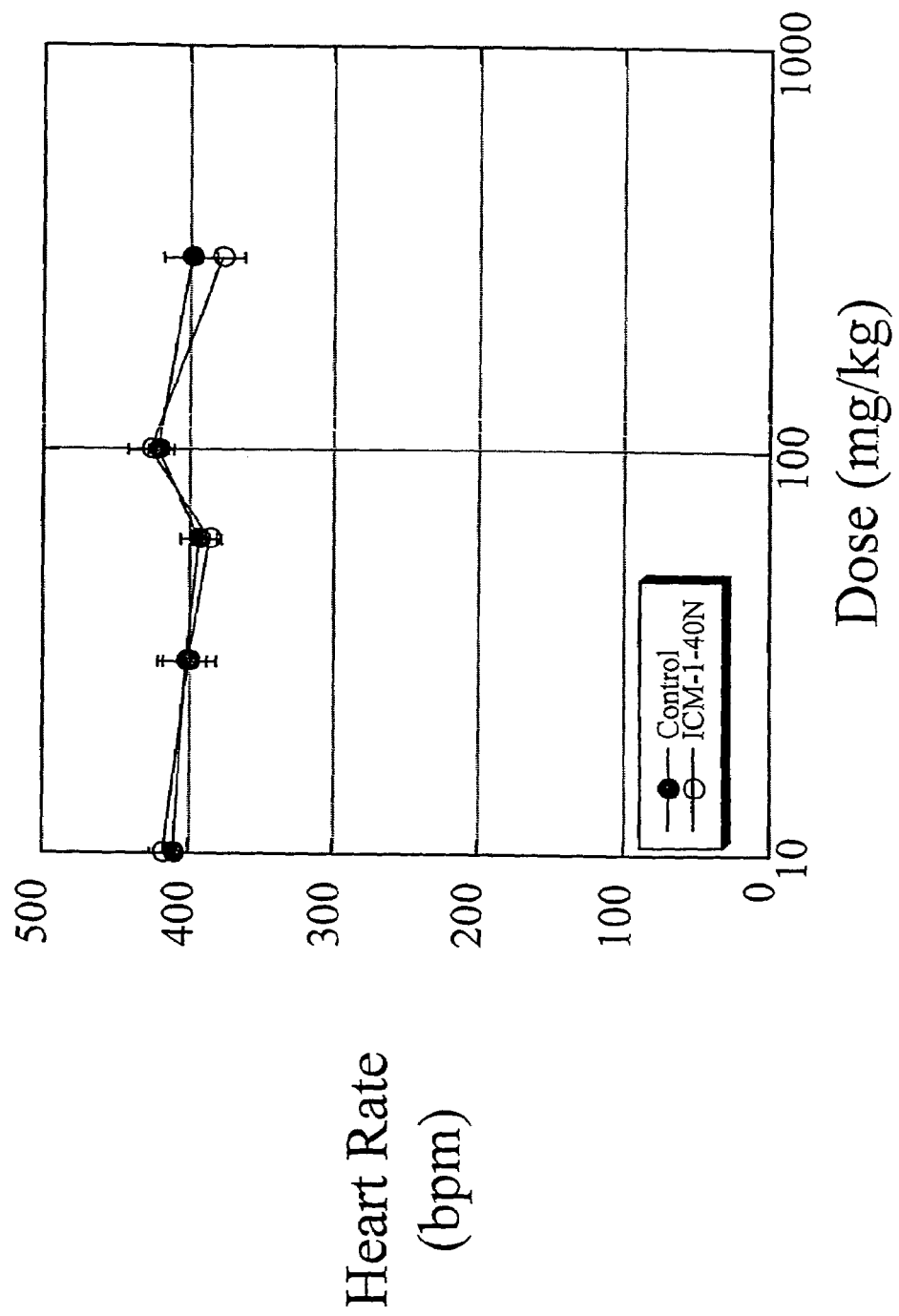
FIG. 6 is a graph plotting the heart rate vs dose and representing the effects of the presence or absence of ICM-I-40N (17) on heart rate during Isoflurane anesthesia.
Figure 7:
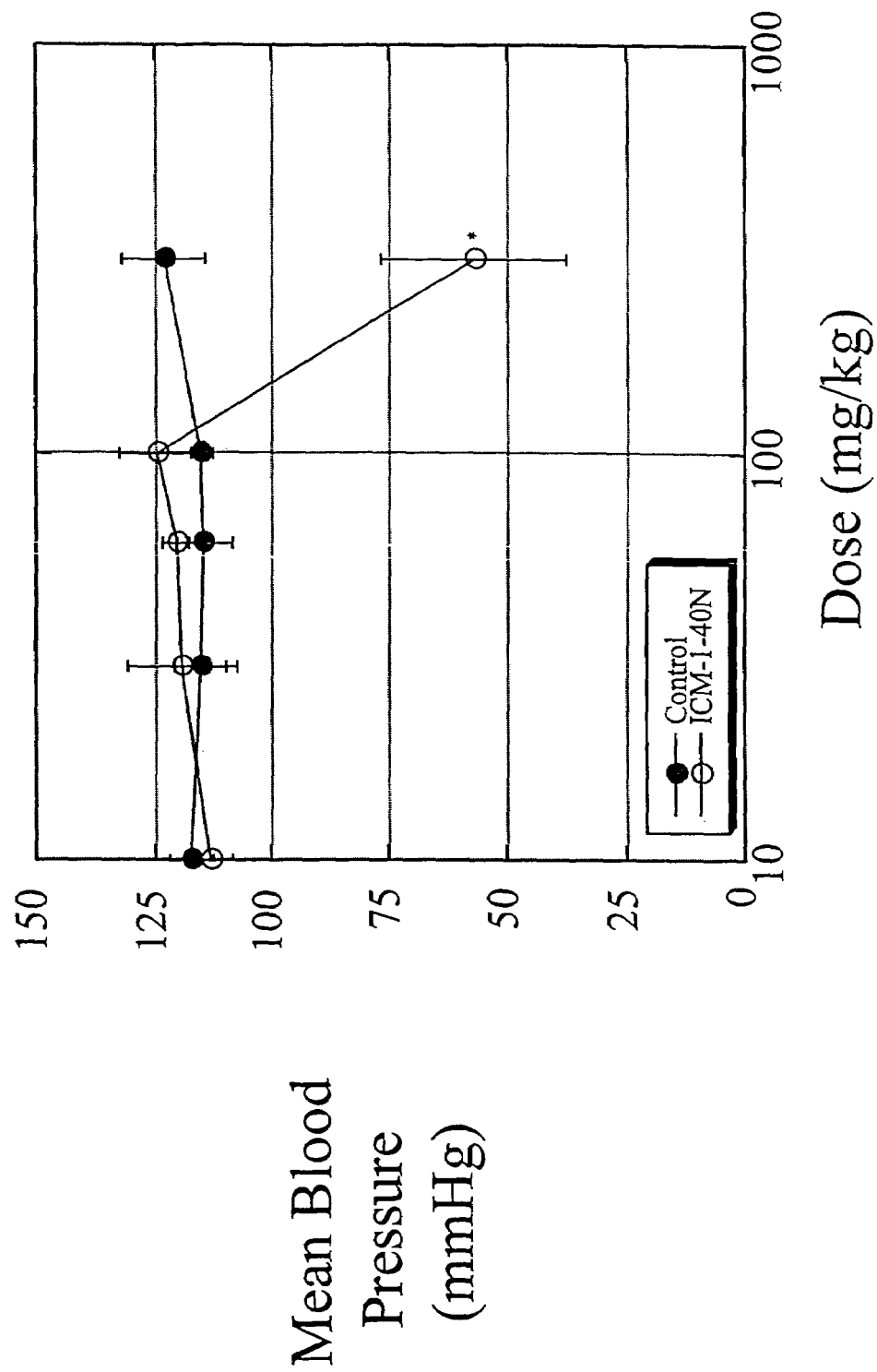
FIG. 7 is a graph plotting the mean blood pressure vs dose and representing the effects of the presence or absence of ICM-I-40N (17) on blood pressure during Isoflurane anesthesia.
Figure 8:
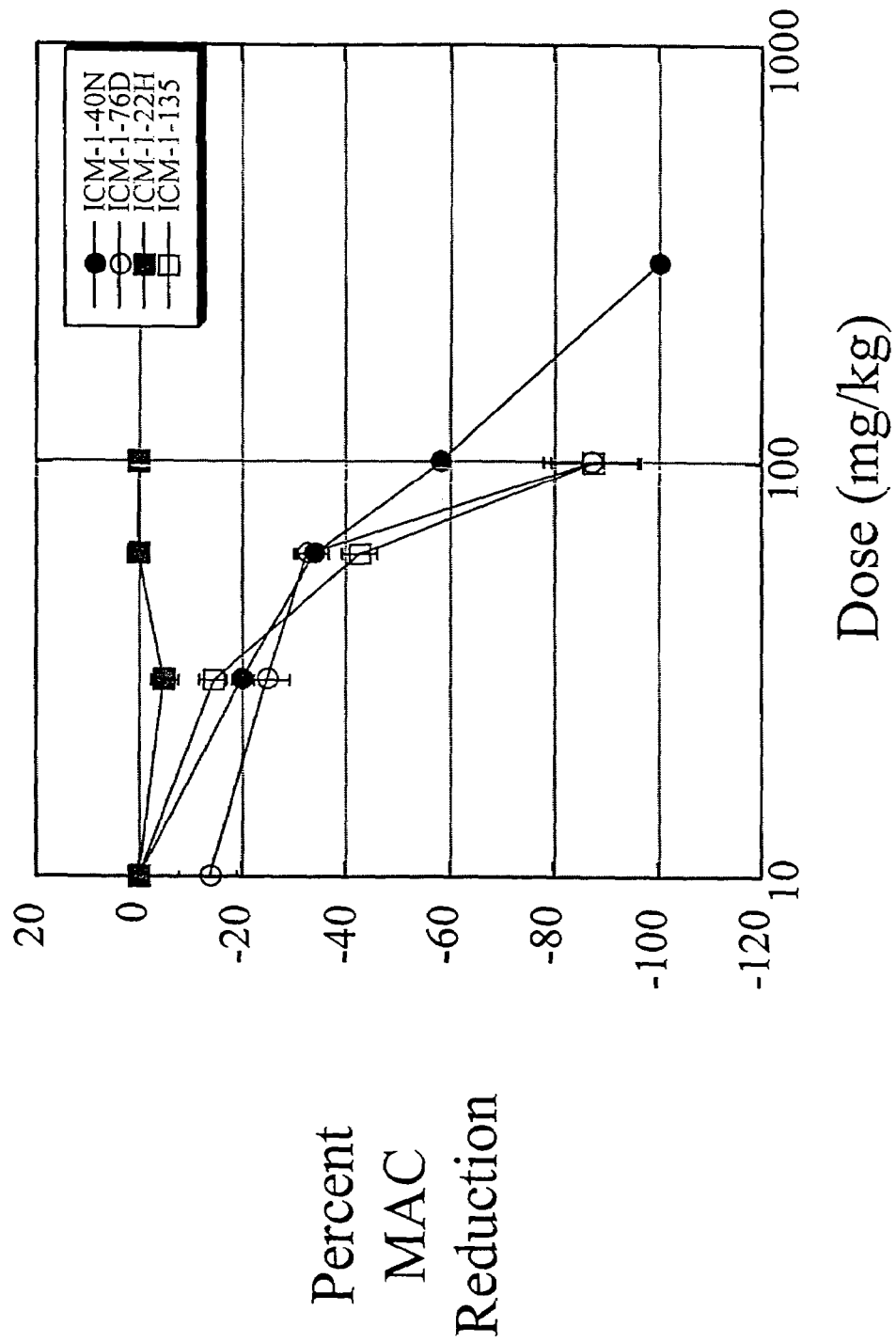
FIG. 8 is a graph plotting the percent MAC reduction vs dose and representing the reduction in the threshold of Isoflurane anesthesia following the administration of ICM-I-40N (●), ICM-1-76D (○), ICM-1-22 (■) and ICM-1-135 (□).

In describing and claiming the invention, the following terminology will be used in accordance with the definitions set forth below.

As used herein, the term "purified" and like terms relate to the isolation of a molecule or compound in a form that is substantially free of contaminants normally associated with the molecule or compound in a native or natural environment.

As used herein, the term "treating" includes prophylaxis of the specific disorder or condition, or alleviation of the symptoms associated with a specific disorder or condition and/or preventing or eliminating said symptoms.

As used herein, the term "halogen" means Cl, Br, F, and I. Especially preferred halogens include Cl, Br, and F. The term "haloalkyl" as used herein refers to a $C_1$-$C_n$ alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n is an integer refers to cyclic non-aryl group, for example $C_3$-$C_8$ cycloalkyl, represents cyciopropyl, cyclobutyl, cyclopentyl, cyclohexyl, cycloheptyl, and cyclooctyl.

The term "lower alkyl" as used herein refers to branched or straight chain alkyl groups comprising one to eight carbon atoms, including methyl, ethyl, propyl, isopropyl, n-butyl, t-butyl, neopentyl and the like.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one to three substituents. The term ($C_5$-$C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "effective amount" means an amount sufficient to produce a selected effect. For example, an effective amount of an anticonvulsant themisone derivative is an amount of the compound sufficient to reduce the incidence of seizures in a patient receiving the dose amount.

The term, "parenteral" means not through the alimentary canal but by some other route such as subcutaneous, intramuscular, intraspinal, or intravenous.

As used herein the term "neurological disease" or "neurological condition" includes neurological related maladies such as spasticity, seizures, depression or mood disorders, neuropathic pain, Alzheimer's Disease, Parkinson's Disease, HIV Dementia and neurological disorders that involve excessive activation of the N-methyl-D-aspartate (NMDA) receptor.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

The MAC value is the minimum alveolar concentration of anesthetic at 1 atm that produces immobility in 50% of the subjects.

The Invention

Previously in the 1950's atrolactamide (themisone) was tested as an anticonvulsant. This compound was found to have anticonvulsant activity but was toxic (blood dyscrasias, rash). Based on applicant's believe that the toxicity of these compounds derived from the formation of the metabolite 2-phenyl-acrylamide, the novel themisone-related compounds of the present invention were prepared that are blocked from the formation of 2-phenyl-acrylamide. With that in mind compound ICM-I-40N (17) was synthesized and evaluated for anticonvulsant activity.

The themisone derivatives of the present invention exhibit similar activities to themisone without the risk of the toxicities associated with themisone administration. Furthermore, applicants have discovered that the themisone derivatives of the present invention also have activity as anesthetics.

In accordance with one embodiment the novel themisone derivatives of the present invention have the general structure:

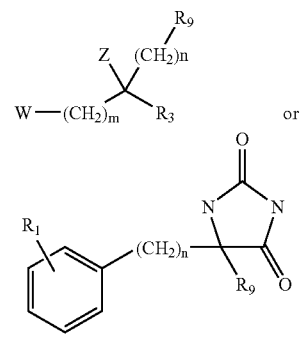

wherein W is selected from the group consisting of alkyl, alkenyl, alkynyl optionally substituted aryl, and optionally substituted heteroaryl;

Z is hydroxy, alkoxy, —$OCOR_{12}$, or, —$COR_{12}$;

$R_1$ is selected from the group consisting of H, halo, $C_1$-$C_4$ haloalkyl, —$NH_2$, hydroxy, and $C_1$-$C_4$ alkoxy;

$R_3$ is aryl, carboxyl, haloalkyl or —($C_1$-$C_4$ alkyl)$NHR_4$, —$CONR_{10}R_4$ or H;

$R_4$ is selected from, the group consisting of $C_1$-$C_4$ alkyl, aryl and H;

$R_{10}$ is H or $C_1$-$C_4$ alkyl;

$R_9$ is optionally substituted aryl or haloalkyl;

$R_{12}$ is $C_1$-$C_4$ alkyl, $NH_2$ or aryl;

m is an integer ranging from 0-3; and n is an integer ranging from 0-1.

More particularly, the present invention is directed to a compound represented by a formula selected from the group consisting of:

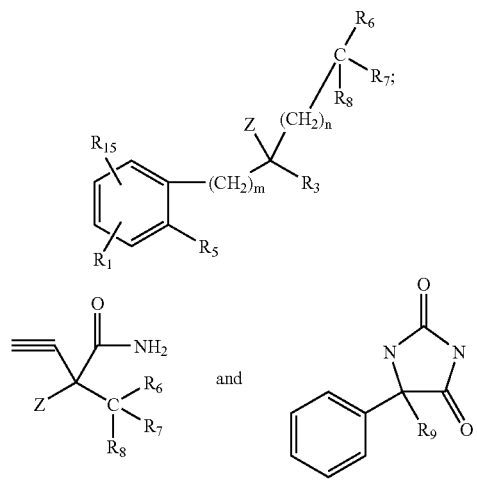

wherein $R_1$ and $R_{15}$ are independently selected from the group consisting of H, halo, $C_1$-$C_4$ haloalkyl, —$NH_2$, hydroxy, and $C_1$-$C_4$ alkoxy;

Z is hydroxy or alkoxy;

$R_3$ is aryl, carboxyl, haloalkyl, —($C_1$-$C_4$ alkyl)$NHR_4$, —$CONR_{10}R_4$ or H;

$R_4$ is selected from the group consisting of $C_1$-$C_4$ alkyl, aryl and H;

$R_5$ and $R_{10}$ are independently H or $C_1$-$C_4$ alkyl, or $R_{10}$ and $R_5$ taken together, can form with the adjacent ring, an optionally substituted 5- or 6-membered heterocyclic ring;

$R_6$, $R_7$ and $R_8$ are independently halo;

$R_9$ is optionally substituted aryl or haloalkyl;

m is an integer ranging from 0-1; and n is an integer ranging from 0-1.

In accordance with one preferred embodiment the themisone derived compound has the general structure:

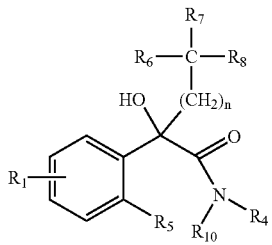

wherein $R_1$ is H or halo;

$R_{10}$ and $R_5$ are independently H, $C_1$-$C_4$ alkyl, or $R_{10}$ and $R_5$ taken together, can form with the adjacent ring, an optionally substituted 5- or 6-membered heterocyclic ring;

$R_4$ is selected from the group consisting of $C_1$-$C_4$ alkyl, aryl and H;

$R_6$, $R_7$ and $R_8$ are independently halo; and n is an integer ranging from 0-1. More preferably, $R_1$ is halo, $R_{10}$, $R_4$ and $R_5$ are H, n is 0; and $R_6$, $R_7$ and $R_8$ are independently selected from the group consisting of F, Cl and Br. In one preferred embodiment the $R_1$ substituent is in the meta or para position and $R_6$, $R_7$ and $R_8$ are each F.

In one embodiment the themisone derivative compound has the general structure:

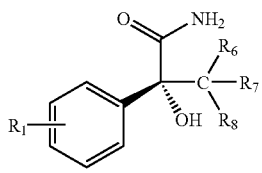

wherein $R_1$ is H or halo; and $R_6$, $R_7$ and $R_8$ are independently selected from the group consisting of F, Cl and Br.

In an alternative embodiment, the themisone derived compound is represented by the formula

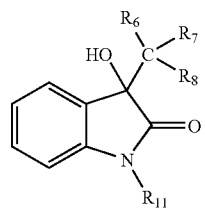

wherein $R_{11}$ is selected from the group consisting of $C_1$-$C_4$ alkyl, aryl and H; and $R_6$, $R_7$ and $R_8$ are independently fluorine or chlorine. In one preferred embodiment, $R_{11}$ is H or $C_1$-$C_4$ alkyl and $R_6$, $R_7$ and $R_8$ are each fluorine In accordance with one embodiment the themisone derivatives of the present invention can be formulated as pharmaceutical compositions by combining the compounds with one or more pharmaceutically acceptable carriers, fillers, solubilizing agents and stabilizers known to those skilled in the art. Such pharmaceutical compositions can be utilized as analgesics, sedatives, anesthetics or as anticonvulsants.

Pharmaceutical compositions comprising the themisone derivatives of the present invention are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means, with oral and intravenous routes being preferred. When administered orally, the compounds can be administered as a liquid solution, powder (lyophilized or otherwise), tablet, capsule or lozenge. Furthermore, oral formulations may include one or more of the present compounds in combination with one or more conventional pharmaceutical additive or excipients that are typically used in the preparation of tablets, capsules, lozenges and other orally administrable forms. When administered as an intravenous solution, the derivatives of the present invention can be admixed with conventional IV solutions to form injectable aqueous or oily suspensions or solutions.

In accordance with one embodiment, the themisone derivatives of the present invention are combined with other known anesthetic agents to enhance the performance of such compounds and decrease the incidence of negative side effects. For example, compositions according to the present invention may comprise a themisone derivative and phencyclidine type general anesthetic such as ketamine or tiletamine and their pharmaceutically acceptable salts, as well as selegiline or one of its pharmaceutically acceptable salts, combined in a single pharmaceutical composition for simultaneous administration, or presented separately for administration in close succession. In the latter case, selegiline has the role of pre-anesthetic or restraining agent. Tiletamine is 2-(ethylamino)-2-(2-thienyl)cyclohexanone. Ketamine is (+−)-2-(2-chlorophenyl)-2-methyl-aminocyclohexanone. Selegiline (−)-N, alpha-dimethyl-N-(2-propynyl)phenethylamine.

The present invention also provides a pharmaceutical pack or kit comprising one or more containers filled with one or more of the themisone derivatives of the present invention. In accordance with one embodiment a kit is provided for anesthetizing a patient. In this embodiment the kit may comprise one or more anesthetic agents of the present invention and as well as other known anesthetic agents and pre-anesthetic or restraining agents. These pharmaceuticals can be packaged in a variety of containers, e.g., vials, tubes, microtiter well plates, bottles, and the like. Preferably, the kits will also include instructions for use.

In one embodiment a composition comprising a themisone derivative of the present invention is used as a general anesthesia in mammals, including both human and domesticated animals. More particularly, compositions comprising the present themisone derivative are administered either orally or parenterally to a mammalian species to induce anesthesia. When administered orally, the compounds are administered as a liquid solution, powder, tablet, capsule or lozenge. The compounds can be used in combination with one or more conventional pharmaceutical additive or excipients used in the preparation of tablets, capsules, lozenges and other orally administrable forms. When administered parenterally, and more preferably by intravenous injection, the derivatives of the present invention can be admixed with saline solutions and/or conventional IV solutions.

In accordance with one embodiment, a method is provided for inducing anesthesia in a human patient. The method comprises the steps of administering to the patient a composition comprising a compound represented by a formula selected from the group consisting of

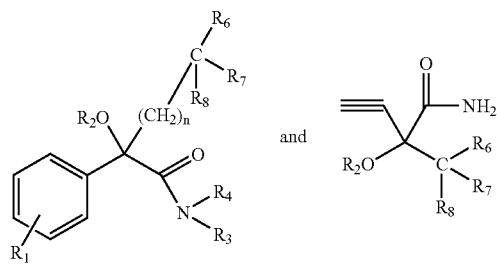

wherein $R_1$ is selected from the group consisting of H, halo, $C_1$-$C_4$ haloalkyl, —$NH_2$, hydroxy, and $C_1$-$C_4$ alkoxy;

$R_2$, $R_3$ and $R_4$ are independently H or alkyl;

$R_6$, $R_7$ and $R_8$ are independently halo; and n is an integer ranging from 0-4, and a pharmaceutically acceptable carrier.

In one preferred embodiment the method of inducing anesthesia in a mammalian species comprising administering a pharmaceutical composition comprising a compound of the general formula:

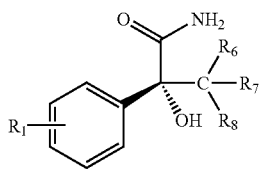

wherein $R_1$ is selected from the group consisting of H or halo and $R_6$, $R_7$ and $R_8$ are independently H or halo, with the proviso that at least one and more preferably two of $R_6$, $R_7$ and $R_8$ are halo. More preferably $R_1$ is F or Br and $R_6$, $R_7$ and $R_8$ are independently F or Cl.

In accordance with one embodiment, a method is provided for treating a neurological condition, including the treatment of seizures. The method comprises the steps of administering to a patient a composition comprising a compound represented by a formula selected from the group consisting of

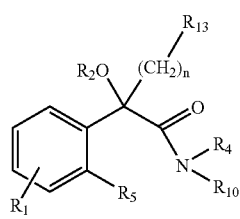

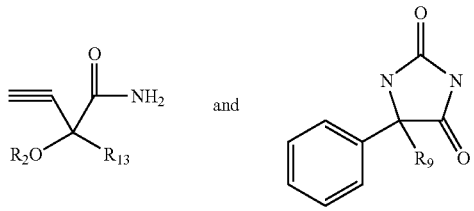

wherein $R_1$ is selected from the group consisting of H, halo, $C_1$-$C_4$ haloalkyl, —$NH_2$, hydroxy, and $C_1$-$C_4$ alkoxy;

$R_2$ and $R_4$ are independently H or alkyl;

$R_{10}$ and $R_5$ are independently H, alkyl, or $R_{10}$ and $R_5$ taken together, can form with the adjacent ring, an optionally substituted 5- or 6-membered heterocyclic ring;

$R_9$ is optionally substituted aryl or haloalkyl; n is an integer ranging from 0-2; and $R_{13}$ is haloalkyl. More preferably, $R_1$ is H or halo, $R_2$ is H and n is 0.

In accordance with one embodiment the method of treating a neurological condition comprises administering a composition comprising a compound of the general formula:

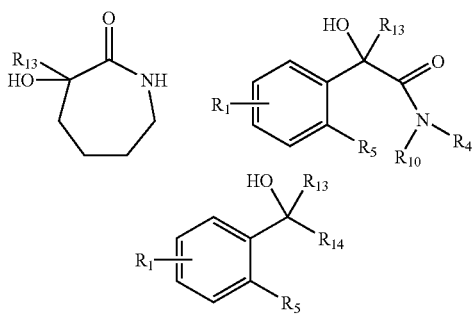

wherein $R_1$ is H or halo;

$R_4$ is H or alkyl;

$R_{10}$ and $R_5$ are independently H, alkyl, or $R_{10}$ and $R_5$ taken together, can form with the adjacent ring, an optionally substituted 5- or 6-membered heterocyclic ring;

$R_{13}$ is haloalkyl; and $R_{14}$ is $C_1$-$C_{12}$ alkyl. More preferably, $R_1$ is H or halo, $R_4$, $R_5$ and $R_{10}$ are H and $R_{14}$ is $C_4$-$C_6$ alkyl. In one embodiment these compounds are administered to a patient as a treatment for reducing the incidence and severity of seizures.

In accordance with the present invention compositions comprising an atrolactamide derivative are administered to a patient to provide neuroprotection in systemic and neurological disease, including neuropathic pain. The compounds can be administered prophylactically, acutely, subacutely, or chronically via the intravenous, oral or rectal route. The compounds of the present invention are anticipated to have activity as analgesics, anti-arrhythmics, mood stabilizers, neuroprotectants and inhibitors of prostate cancer.

In accordance with one embodiment, the hydrogens of the 2-methyl group substituent of themisone are substituted with halo groups to prevent the elimination reaction and formation of 2-phenyl-acrylamide. For example, the hydrogens can be replaced with fluorine to create 3,3,3-Trifluoro-2-hydroxy-2-phenyl-propionamide (17). Fluorine is an classic mimic for hydrogen, with the two elements having similar Van der Waals radii, 1.20 and 1.35 angstroms, respectively.

Anticonvulsant testing of 3,3,3-Trifluoro-2-hydroxy-2-phenyl-propionamide (17) in rats revealed the compounds have anesthetic activity at an oral $ED_{50}$ of 9 mg/kg and toxicity at 300 mg/kg. Further testing in UVa's Department of Anesthesiology revealed the fluorinated derivative lowered the minimum alveolar concentration (MAC) value of isoflurane (1.2% in $O_2$) by sixty percent, with no hemodynamic effects. Furthermore, testing of 3,3,3-Trifluoro-2-hydroxy-2-(4-fluoro-phenyl)-propionamide (39) revealed this compound provided 3 out of 4 animals with a 100% reduction in Isoflurane MAC at 300 mg/kg. The tested animals exhibited surgical anesthesia, the third stage of anesthesia displayed by general loss of spinal reflexes and muscle tone. Themisone was later tested and found to have no anesthetic activity. Other themisone compounds have now been tested and found to exhibit both anticonvulsant and anesthetic activities as described in the following examples.

Compound 39 also demonstrated activity as an anticonvulsant both in the MES and scMET assays (See Example 3). In particular, in phase I oral rat data generated with MES, 4 out of 4 rats were protected using 30 mg/kg for a duration of 2 hours. In phase I intraparentoneal data for MES 2 out of 3 mice were protected at 100 mg/kg for a duration of 1 hour and 5 out of 5 mice were protected at 100 mg/kg for a duration of 0.5 hours. Neurotoxicity revealed that seven of eight mice were unable to grasp rod at 100 mg/kg for a duration of 0.5 hours.

EXAMPLE I

Structure Activity Relationship (SAR) of
3,3,3-Trifluoro-2-hydroxy-2-phenyl-propionamide
Using Ligand Based Design In accordance with one embodiment of the present invention, the formation of 2-phenyl-acrylamide is blocked by replacing the hydrogens of the 2-methyl group substituent of themisone with compounds that prevent the elimination reaction. For example, the hydrogens can be replaced with fluorine to create 3,3,3-Trifluoro-2-hydroxy-2-phenyl-propionamide (17).

Anticonvulsant testing of 3,3,3-Trifluoro-2-hydroxy-2-phenyl-propionamide (17) in rats revealed that in addition to exhibiting anticonvulsant activity, this themisone derivative has anesthetic activity at an oral $ED_{50}$ of 9 mg/kg and toxicity at 300 mg/kg. Themisone was later tested and found to have no anesthetic activity. Animals administered 3,3,3-Trifluoro-2-hydroxy-2-phenyl-propionamide (17) exhibited surgical anesthesia, the third stage of anesthesia displayed by general loss of spinal reflexes and muscle tone. Further testing in UVa's Department of Anesthesiology revealed the fluorinated derivative lowered the minimum alveolar concentration (MAC) value of isoflurane (1.2% in $O_2$) by sixty percent, with no hemodynamic effects. In general for compound 17 investigation of structure to general anesthetic relationship revealed that the phenyl ring conformation of 17 is important and that para-electron withdrawing groups increase the anesthetic activity of the compound. In addition increased halogen size and saturation at the position 3 carbon also increase anesthetic activity. A hydrogen bond donor is also important at the position 2 carbon, but bulk is not well tolerated.

To investigate the activity of various 3,3,3-Trifluoro-2-hydroxy-2-phenyl-propionamide related compounds, the following derivative compounds will be prepared:

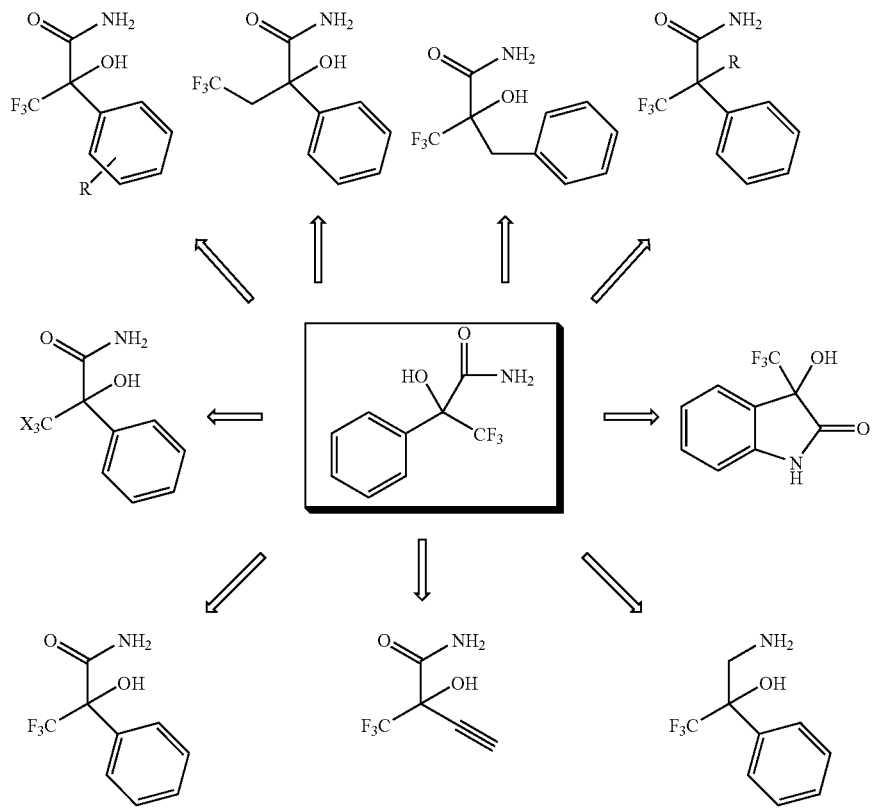

It is anticipated that these derivatives will provide an orally available general anesthetic that is capable of inducing anesthesia smoothly and rapidly, allow rapid recovery, and pose a wide margin of safety (high therapeutic index). These compounds are also expected to exhibit dual anticonvulsant activity. Synthesis of the dual anticonvulsants and general anesthetics began with the hydroxyamides of the commercially available phenyl substituted trifluoro-methyl ketones.

Scheme I

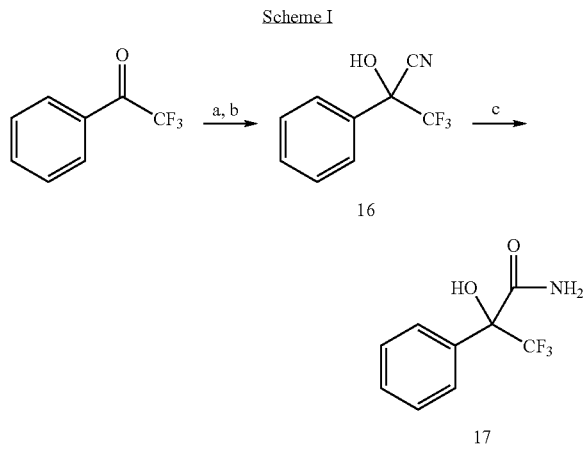

Reaction conditions: a: TMSCN, TiCl$_4$, CH$_2$Cl$_2$; b: H$_2$O; c: 1,4-dioxane, conc. HCl, HCl gas.

Similarly, the synthetic scheme for preparing meta-F, para-Cl derivatives is shown in scheme II, respectively:

Scheme II

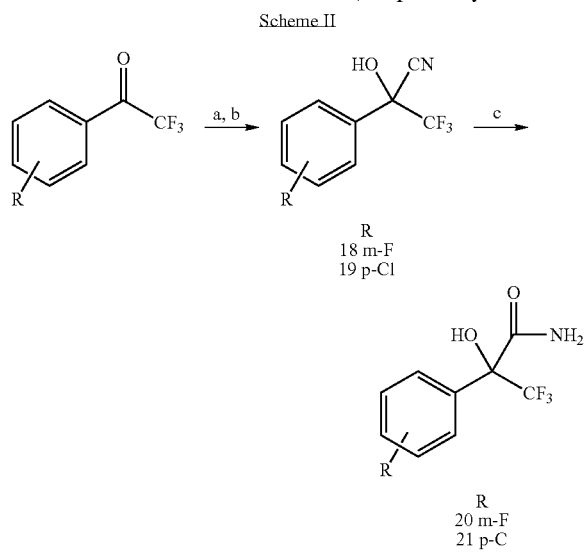

Reaction conditions: a: TMSCN,ZnI$_2$, CH$_2$Cl$_2$; b: 15% HCl, THF; c: 1,4-dioxane, conc. HCl, HCl gas.

Closed ring analogs of the lead compound were synthesized by the use of TMS-CF$_3$ (see Scheme III). Several attempts had been made to synthesize the compound with the use of tetrabutylammonium fluoride (TBAF). The trimethylsilyl ether intermediate was found to be very stable and difficult to quench with varying amounts of acid. The exothermic reaction of a catalytic amount of KF, and saturated t-BuOK in THF, was found to produce the desired product, although in low yield with unprotected amides.

Scheme III

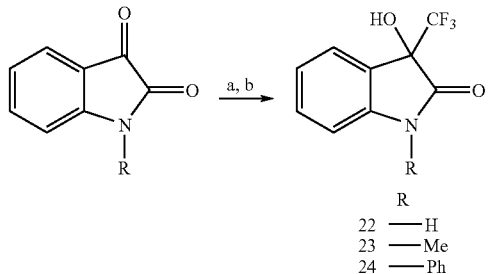

Reaction Conditions: a: TMS-CF3, KF, t-BuOK, THF; b: 15% HCl

N-trifluoroacetylpiperdine 25 was reacted with 0.8 equivalents of 4-Bromoanisole to yield 26 (see Scheme IV). All other ketones can now be synthesized to yield all the remaining hydroxyamides with the use of TMS-CN, followed by HCl gas.

Scheme IV

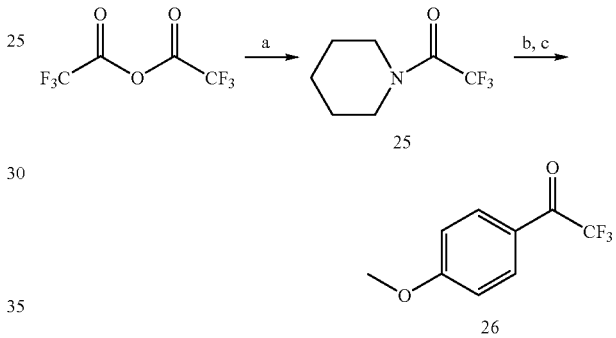

Rxn Conditions: a: piperdine, Et$_3$N, Ether; b: 4-Bromoanisole, Mg, I$_2$, THF; c: NH$_4$Cl Halogenation of general anesthetics stabilizes the compounds and reduces metabolism. We hypothesized that changes in the haloform content could have an affect on potency, duration and hemodynamic activity. The chlorinated cyanohydrin 28 was successfully made (see Scheme V), although several attempts to synthesize the hydroxyamide were unsuccessful. Under acidic conditions such as HCl and HCl gas, or formic acid and HCl gas converted the cyanohydrin back to the starting ketone. Other unsuccessful attempts included K$_2$CO$_3$ and 30% H$_2$O$_2$, and UHP and K$_2$CO$_3$. A new synthetic scheme is now being evaluated starting with the acid chloride, trichloroacetyl chloride (see Scheme VI). The brominated ketone was made, although in low yield (see Scheme VII). Several attempts to form the cyanohydrin, with the use of TMS-CN and various catalysts were unsuccessful. It is believed that steric hinderance plays a large role in the difficulty of synthesizing these two hydroxyamides.

Scheme V

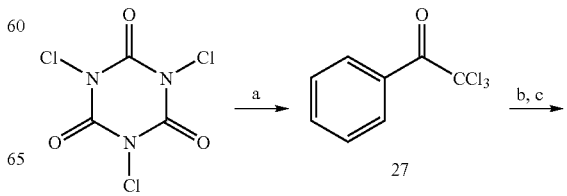

15

-continued

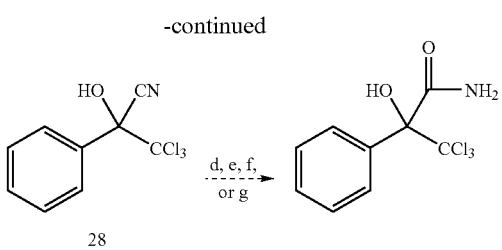

28

Reaction Conditions: a: acetophenone, acetic acid, reflux, 8 hrs.; b: TMS-CN, THF, reflux, 12 hrs.; c: 15% HCl; d: conc. HCl, HCl gas; e: formic acid, HCl gas; f: $K_2CO_3$, 30% $H_2O_2$; g: UHP, $K_2CO_3$.

Scheme VI

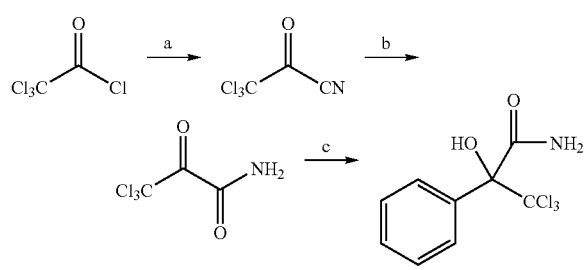

Reaction Conditions: a: KCN, 18-crown-6, $CH_2Cl_2$; b: DMSO, $K_2CO_3$, 30% $H_2O_2$; c: $ZnPh_2$ Scheme VII

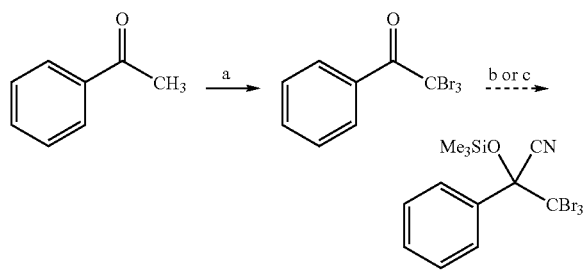

Reaction Conditions: a: $Br_2$, NaOH, $H_2O$, 1,4-dioxane, 0° C. to RT; b: TMS-CN, $ZnI_2$, $CH_2Cl_2$; c: TMS-CN, KCN, 18-crown-6, $CH_2Cl_2$.

200 mg of each compound are tested for general anesthesia activity Testing is performed on rats to determine the percent reduction in the use of isoflurane. Inhaled anesthetics still need to be utilized to rapidly adjust the level of anesthesia. Since no single anesthetic is capable of all four requirements for anesthesia, a combination is utilized. The rats were first anesthetized with isoflurane, intubated, ventilated and then a femoral line was inserted. After the rat had been stable for 15 minutes, the initial minimum alveolar concentration (MAC) value was determined. Then, 60 mg/kg of drug was sonicated in 3 mL of peanut oil and injected (i.p.). After 30 minutes the second MAC value was determined post administration. Finally, after one hour the third MAC value was determined. At each MAC determination, a sample of blood was taken to determine pH, $pCO_2$, and $pO_2$. The results of the compounds tested to date are compared to the lead compound 17.

A classical comparison of log P and MAC reduction was investigated. A graph representing the effects of log P on the biological activity is presented in graphic form (See FIG. 1). The general anesthetic activity of compounds 20-23 and 36-43 were compared to lead compound 17 as represented in the graph (FIG. 1) and in Table 1. The partition coefficient, P, is a measure of the way the compound distributes itself between octanol and water. The graph displays a general parabola shape with an optimal log P value of approximately 1.5, since compounds 20 and 42 were very toxic, despite their high activity. Compounds 20 and 42 also had a low lethal dose of 300 mg/kg. Derivatives with para-substituted phenol ring derivatives 21 and 39 were found to be very active, but also toxic at the same dosage. Therefore, meta-substituted derivatives 20 will be the focus of future synthesize. Bulky substituents on the alcohol were also found to have low activity. Closed ring analogs are active at lower levels but cause no hemodynamic effects.

TABLE 1

| Compound | MAC value of Isoflurane at 60 mg/kg of compound* | Percent Reduction in Isoflurane | Hemodynamic Effects | Log P |
|---|---|---|---|---|
| 17 | 0.65 | 46 | none | 1.26 |
| 20 | 0.70 | 42 | lowers blood pressure | 1.82 |
| 21 | 0.65 | 46 | none | 1.42 |
| 22 | 1.05 | 12.5 | none | 1.13 |
| 23 | 0.95 | 20.8 | none | 1.36 |

*1.2% isoflurane generates 100% anesthesia;
log P calculated using by Crippen's fragmentation: J.Chem.Inf.Comput.Sci., 27, 21(1987) in ChemDraw Ultra

EXAMPLE 2

The phenyl-substituted caprolactams have been found to be very active anticonvulsants. Therefore, the —$CF_3$ moiety was added to the seven membered ring carpolactam (see Scheme VIII) and these compounds are anticipated to have activity as anticonvulsants. -Caprolactam is alpha brominated with bromine and phosphorus pentachloride. Formation of the enamine 31 is accomplished with 30 refluxed in piperdine for 6 hours. Cleavage of the enamine is done on a silica gel column eluted with ethyl acetate. Due to the low yield of 32 the amide was protected before the reaction with TMS-$CF_3$. There were several unsuccessful attempts to protect the amide, using benzyl bromide and various bases.

Scheme VIII

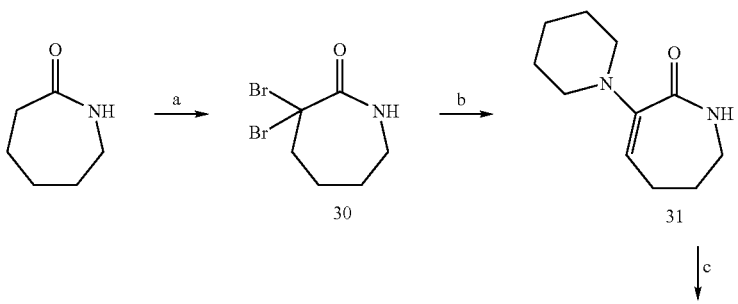

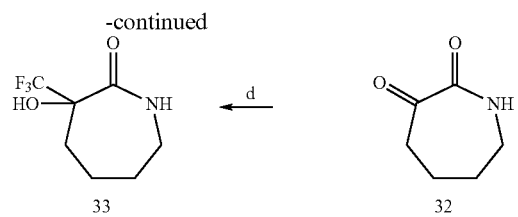

Reaction Conditions: a:Br$_2$, PCl$_5$, CHCl$_3$; b: piperdine, reflux, 6 hrs.; c: silica gel EtOAc; d: TMS-CF$_3$.

EXAMPLE 3

Anticonvulsant Properties of the Themisone Derivative Compounds

To investigate the anticonvulsant properties of the themisone derivatives, synthesis of the seven chain carbon hydroxyamides with substituted chlorine and methoxy groups on the phenyl ring were prepared in accordance with scheme IX. These derivatives were made-as anticonvulsants and were not predicted to be active general anesthetics.

Scheme IX

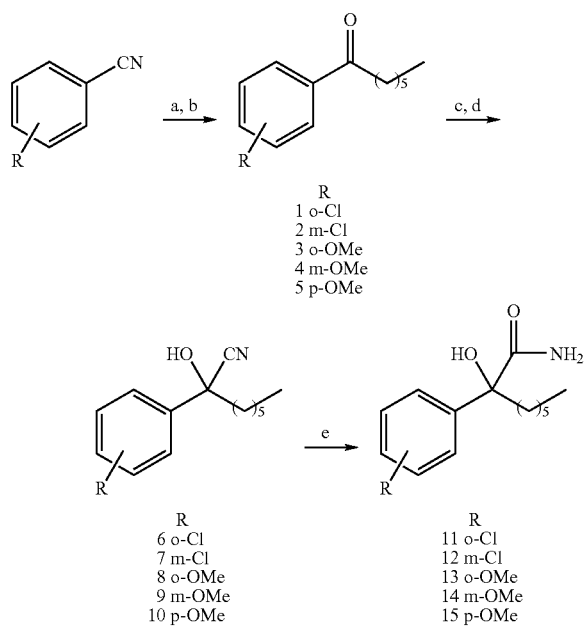

Reaction Conditions: a: 1-Bromoheptane, Mg, I$_2$, THF; b: 15% HCl; c: TMSCN, ZnI$_2$, CH$_2$Cl$_2$; d: 15% HCl, THF; e: 1,4-dioxane, conc. HCl, HCl gas.

300 mg of each compound was synthesized and sent to the National institute of Health's Anticonvulsant Screening Project of the Antiepileptic Drug Discovery Program. NIH performs anticonvulsant testing (oral and intraperitoneal, i.p.) on both mice and rats in phase I trials. The grand mal model is conducted with a maximal electroshock (MES) test, where corneal electrode implants are primed with a drop of electrolyte solution and an electrical stimulus is delivered for 0.2 second. The model examines the compounds' ability to stop the spread of seizures. The petite mal model is conducted with a subcutaneous pentylenetetrazol seizure threshold (scMet) test. The animals are injected with a convulsant dose of pentylenetetrazol at the peak effect time of the compound. This model measures the compounds' threshold for seizures. A toxicity test (TOX) is performed where the animals walk on a spinning rod for varying lengths of time to check for the loss of righting reflex or other toxic effects. Phase I evaluation at 30, 100 and 300 mg/kg of test compounds has resulted in several newly discovered active anticonvulsants (See FIGS. 2-5).

One important aspect of central nervous system drug delivery is brain distribution. Derivatives of phenytoin were designed and synthesized with fluorine tags (see scheme IX). The compounds were tested using the kindling model to access their anticonvulsant activity. Rats with the injected drugs will then be exposed to $^{19}$F magnetic resonance imaging (MRI) to study the drug distribution in the brain of a known compound. The model will then be used as a model to test the active fluorinated compounds.

Scheme X

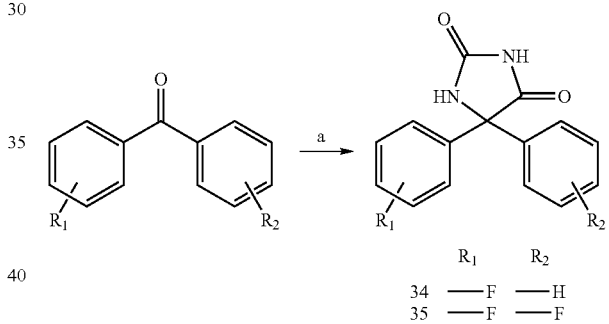

Reaction Conditions: a: KCN, (NH4)2CO3, 50% EtOH, 65° C., 24 hrs.

TABLE 2

Anticonvulsant Testing (NIH) Mice I.P. Administration

| Test | Dose (mg/kg) | Cmp 20 Time (0.5 hours) | Cmp 20 Time (4.0 hours) | Cmp 21 Time (0.5 hours) | Cmp 21 Time (4.0 hours) | Cmp 23 Time (0.5 hours) | Cmp 23 Time (4.0 hours) |
|---|---|---|---|---|---|---|---|
| MES | 30 | 0/1[a] | 0/1 | 0/1 | 0/1 | 0/1 | 0/1 |
| MES | 100 | 3/3 | 3/3 | 0/3 | 1/3 | 3/3 | 0/3 |
| MES | 300 | 0/0 | 1/1 | n/a | n/a | 1/1 | 1/1 |
| SCMET | 30 | 2/5 | 0/1 | 0/1 | 0/1 | 1/5 | 0/1 |
| SCMET | 100 | 1/1 | 1/1 | 4/4 | 1/1 | 0/1 | 1/1 |
| SCMET | 300 | n/a | n/a | 0/0 | 1/1 | 1/1 | 1/1 |
| TOX | 30 | 0/4 | 0/2 | 0/4 | 0/2 | 0/4 | 0/2 |
| TOX | 100 | 6/8 | 0/4 | 6/8 | 3/4 | 1/8 | 0/4 |
| TOX | 300 | 4/4[b] | 1/1[c] | 4/4[b] | 1/1[c] | 4/4[c] | 1/2 |

[a] 0/1 refers to number of animals protected/number of animals tested
[b] loss of righting reflex and one death
[c] loss of righting reflex

TABLE 3
Anticonvulsant Testing (NIH)
Rat Oral Administration - Compound 21
| Test | Dose (mg/kg) | 0.25 hrs. | 0.5 hrs. | 1.0 hrs. | 2.0 hrs. | 4.0 hrs. |
|---|---|---|---|---|---|---|
| MES | 30 | 1/4 | 1/4 | 1/4 | 1/4 | 1/4 |
| TOX | 30 | 0/4 | 0/4 | 0/4 | 0/4 | 0/4 |
TABLE 4
Anticonvulsant Testing (NIH)
Rat Oral Administration - Compound 23
| Test | Dose (mg/kg) | 0.25 hrs. | 0.5 hrs. | 1.0 hrs. | 2.0 hrs. | 4.0 hrs. |
|---|---|---|---|---|---|---|
| MES | 30 | 2/4 | 1/4 | 2/4 | 2/4 | 2/4 |
| TOX | 30 | 0/4 | 0/4 | 0/4 | 0/4 | 0/4 |
EXAMPLE 4
Additional Synthetic Schemes
Scheme XI
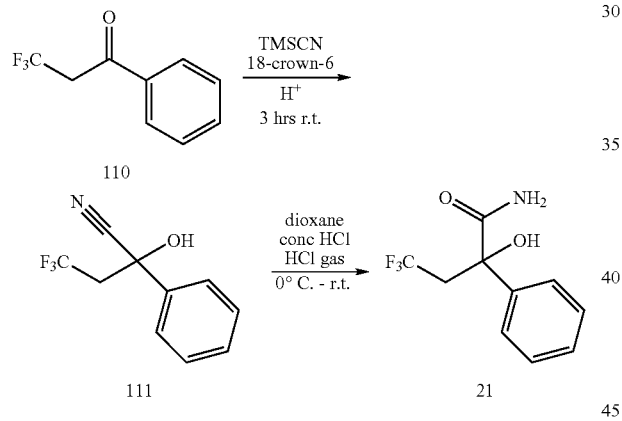
Scheme XII
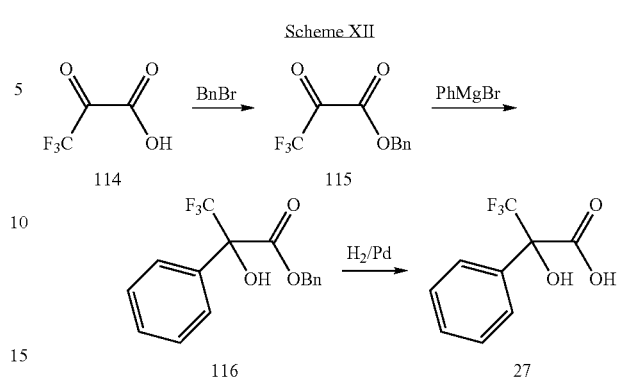
Scheme XIII
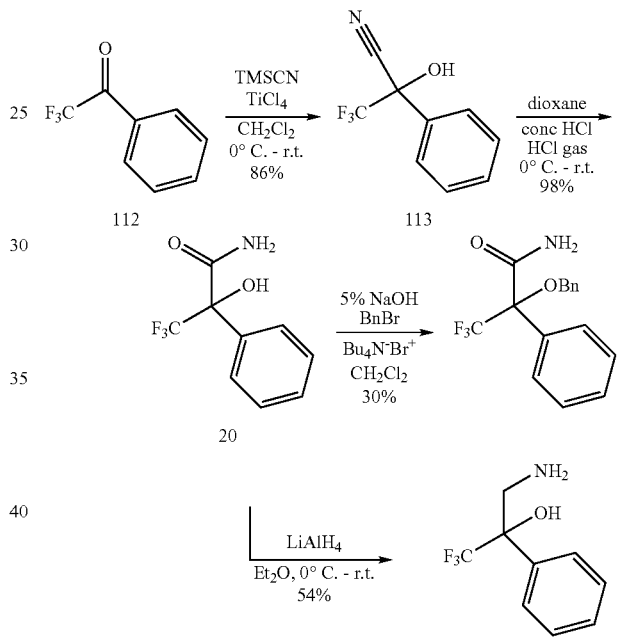
Scheme XIV
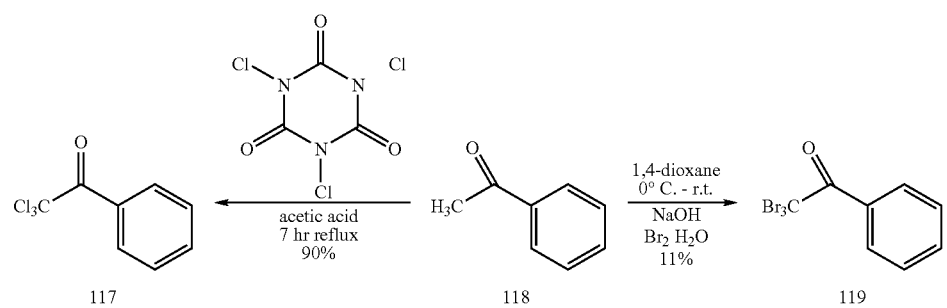

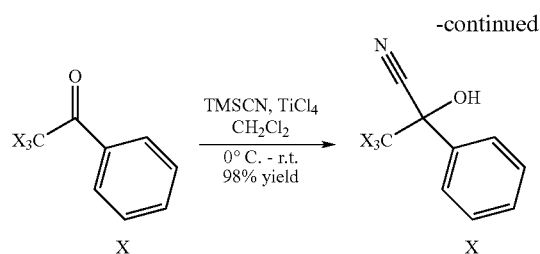
| X | |
|---|---|
| 120 | H₃ |
| 121 | Br₃ |
| 122 | ClF₂ |
| 123 | Cl₃ |
| X | |
|---|---|
| 124 | H₃ |
| 125 | Br₃ |
| 126 | ClF₂ |
| 127 | Cl₃ |
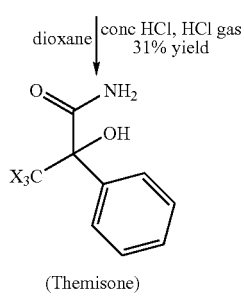
(Themisone)
| X | |
|---|---|
| 128 | H₃ |
| 28 | Br₃ |
| 29 | ClF₂ |
| 30 | Cl₃ |
Scheme XV
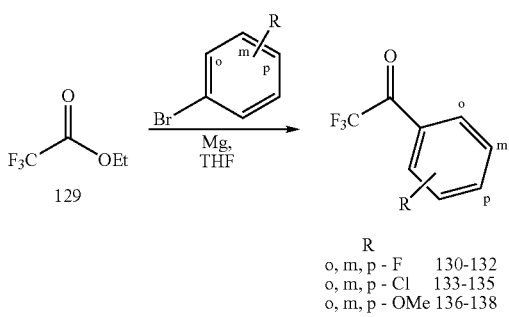
| R | |
|---|---|
| o, m, p - F | 130-132 |
| o, m, p - Cl | 133-135 |
| o, m, p - OMe | 136-138 |
Scheme XVI
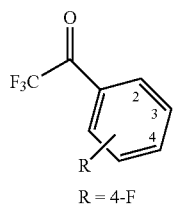
R = 4-F
139
| R | |
|---|---|
| o, m - F | 141-142 |
| o, m, p - Cl | 143-145 |
| o, m, p - oMe | 146-148 |
TMSCN, TiCl₄
CH₂Cl₂, 0° C. - r.t.
100%
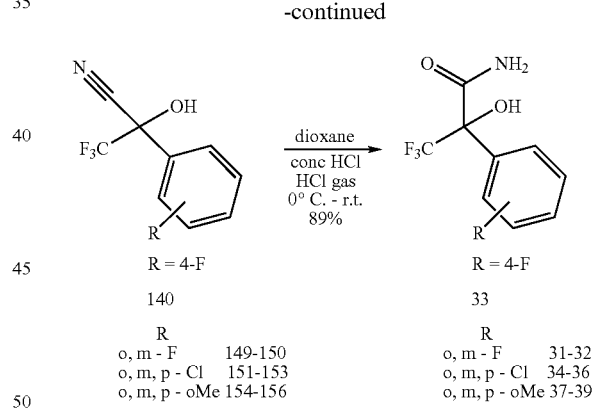
R = 4-F
140
| R | |
|---|---|
| o, m - F | 149-150 |
| o, m, p - Cl | 151-153 |
| o, m, p - oMe | 154-156 |
R = 4-F
33
| R | |
|---|---|
| o, m - F | 31-32 |
| o, m, p - Cl | 34-36 |
| o, m, p - oMe | 37-39 |
Synthesized themisone derivatives:
ICM-I-40N
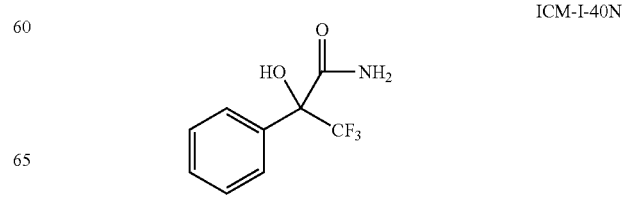

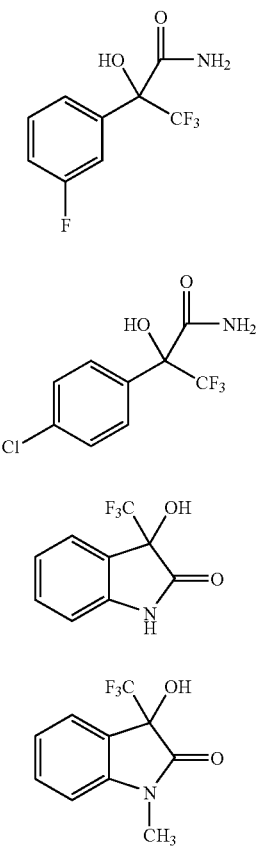
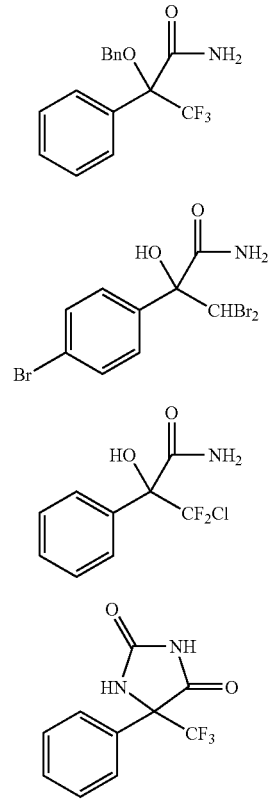
Themisone
The invention claimed is:
1. A compound represented by the formula:
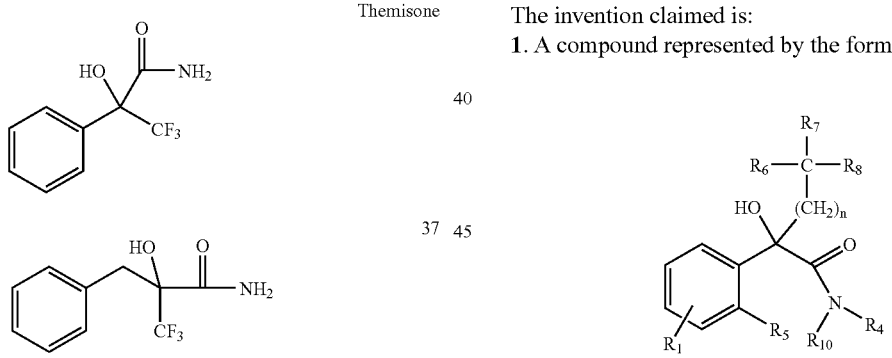
wherein $R_1$ is halo, and located in the meta or para position;
$R_{10}$, $R_4$ and $R_5$ are H;
n is 0; and
$R_6$, $R_7$ and $R_8$ are each F.
2. A compound represented by the formula:
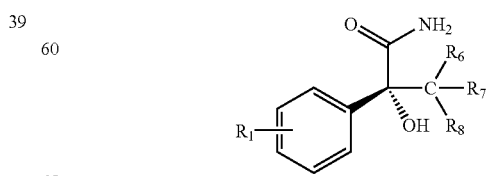
wherein $R_1$ is halo, and $R_6$, $R_7$ and $R_8$ are F.

3. A compound is represented by the formula:

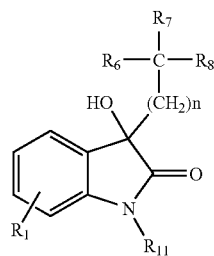

wherein $R_1$ is halo;
$R_6$, $R_7$ and $R_8$ are F;
$R_{11}$ is selected from the group consisting of $C_1$-$C_4$ alkyl and aryl; and
n is 0.

4. A pharmaceutical composition comprising a compound of claim 1 and a pharmaceutically acceptable carrier.

5. The composition of claim 4 further comprising selegiline.

6. A compound represented by a formula selected from the group consisting of

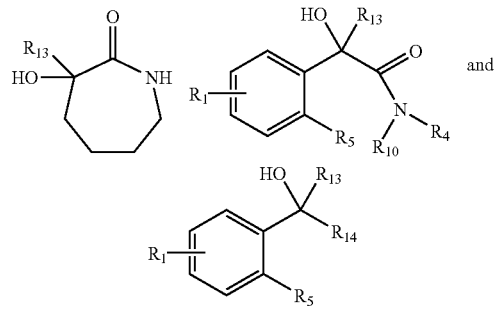

wherein $R_1$ is halo;
$R_4$, $R_5$ and $R_{10}$ are H;
$R_{13}$ is $CF_3$; and
$R_{14}$ is $C_4$-$C_6$ alkyl.

7. A pharmaceutical composition comprising a compound of claim 2 and a pharmaceutically acceptable carrier.

8. The composition of claim 7 further comprising selegiline.

* * * * *